United States Patent [19]

Meier et al.

[11] Patent Number: 4,512,997

[45] Date of Patent: Apr. 23, 1985

[54] 4,5-BIS(ARYL)-4H-1,2,4-TRIAZOLE DERIVATIVES AND ANALGESIC USE

[75] Inventors: Jean Meier, La Varenne Saint Hilaire; Francois Clemence, Paris, both of France

[73] Assignee: Roussel Uclaf, Paris, France

[21] Appl. No.: 552,747

[22] Filed: Nov. 17, 1983

Related U.S. Application Data

[63] Continuation of Ser. No. 292,790, Aug. 14, 1981, abandoned.

[30] Foreign Application Priority Data

Aug. 22, 1980 [FR] France ................................ 80 18354

[51] Int. Cl.³ .................. A61K 31/395; C07D 249/08
[52] U.S. Cl. ............................. 514/383; 260/544 D; 260/544 N; 548/262; 564/74; 564/148; 564/149; 564/150; 564/151; 564/226; 549/436
[58] Field of Search ......................... 548/262; 424/269

[56] References Cited

U.S. PATENT DOCUMENTS

| | | | |
|---|---|---|---|
| 1,796,403 | 3/1931 | Scheuing et al. | 548/262 |
| 3,681,374 | 8/1972 | Yano et al. | 548/262 |
| 4,038,405 | 7/1977 | Evans | 424/269 |

OTHER PUBLICATIONS

Reimlinger et al, Chem. Abstracts, vol. 74, Abstract 87,898 (1971).
Kendall et al, Chem. Abstracts, vol. 51, cols. 16162-16163 (1957).
Spasov et al, Chem. Ber., 1969, vol. 102, pp. 2530-2535.
Huisgen et al, Chem. Ber., 1960, vol. 93, pp. 2885-2891.
Beilstein's Handbuch der Organischen Chemie, vol. 26, Zweites Erganzungswerk (Vierte Auflag, Berlin, 1954), p. 35.

*Primary Examiner*—Alton D. Rollins
*Attorney, Agent, or Firm*—Charles A. Muserlian

[57] ABSTRACT

Novel 4H-1,2,4-triazoles of the formula

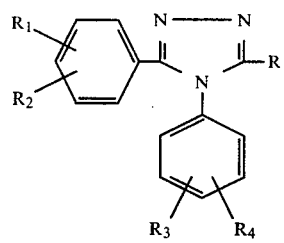

wherein $R_1$, $R_2$, $R_3$ and $R_4$ may be in different positions of the benzene rings and are individually selected from the group consisting of hydrogen, —OH, alkyl of 1 to 4 carbon atoms, alkoxy of 1 to 4 carbon atoms, halogen, —$CF_3$, —$NO_2$, —$NH_2$ and —NH—AlK and

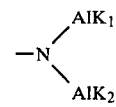

and AlK, $AlK_1$ and $AlK_2$ are alkyl of 1 to 4 carbon atoms or $R_1$ and $R_2$ together and/or $R_3$ and $R_4$ together are methylenedioxy, R is selected from the group consisting hydrogen, alkyl of 1 to 4 carbon atoms, —$CH_2$—COOH and —$CH_2$—COO$AlK_3$ and $AlK_3$ is alkyl of 1 to 4 carbon atoms and their non-toxic, pharmaceutically acceptable acid addition salts having a remarkable analgesic activity and a novel method for their preparation.

28 Claims, No Drawings

4,5-BIS(ARYL)-4H-1,2,4-TRIAZOLE DERIVATIVES AND ANALGESIC USE

PRIOR APPLICATION

This application is a continuation of copending U.S. patent application Ser. No. 292,790 filed Aug. 14, 1981, now abandoned.

STATE OF THE ART 1,2,4-triazoles useful as intermediates in the synthesis of compounds are described in J. Chem. Soc., 1954, p. 4257, Tet. Letters, No. 47, Nov. 1978, p. 4629–4632 and Chem. Ab., Vol. 54, No. 1 (1960), p. 2333h.

OBJECTS OF THE INVENTION

It is an object of the invention to provide the novel 4H-1,2,4-triazoles of formula I and their non-toxic, pharmaceutically acceptable acid addition salts and a novel process and novel intermediates for their preparation.

It is another object of the invention to provide novel analgesic compositions and a novel method of relieving pain in warm-blooded animals.

These and other objects and advantages of the invention will become obvious from the following detailed description.

THE INVENTION

The novel products of the invention are selected from the group consisting of 4H-1,2,4-triazoles of the formula

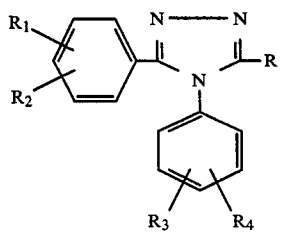

wherein $R_1$, $R_2$, $R_3$ and $R_4$ may be in different positions of the benzene rings and are individually selected from the group consisting of hydrogen, —OH, alkyl of 1 to 4 carbon atoms, alkoxy of 1 to 4 carbon atoms, halogen, —$CF_3$, —$NO_2$, —$NH_2$ and —NH—AlK and

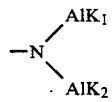

and AlK, $AlK_1$ and $AlK_2$ are alkyl of 1 to 4 carbon atoms or $R_1$ and $R_2$ together and/or $R_3$ and $R_4$ together are methylenedioxy, R is selected from the group consisting of hydrogen, alkyl of 1 to 4 carbon atoms, —$CH_2$—COOH and —$CH_2$—$COOAlK_3$ and $AlK_3$ is alkyl of 1 to 4 carbon atoms and their non-toxic, pharmaceutically acceptable acid addition salts.

Examples of suitable acids to form the non-toxic pharmaceutically acceptable acid addition salts are inorganic acids such as hydrochloric acid, hydrobromic acid, sulfuric acid and phosphoric acid and organic acids such as acetic acid, propionic acid, maleic acid, hemisuccinic acid, etc.

When R, $R_1$, $R_2$ and $R_4$ are alkyl, they are preferably methyl, ethyl, n-propyl, isopropyl or n-butyl. $AlK_1$, $AlK_2$, $AlK_3$ and AlK are preferably methyl, ethyl, n-propyl, isopropyl or n-butyl. When $R_1$, $R_2$, $R_3$ or $R_4$ are halogen, they may be fluorine, chlorine, bromine or iodine, preferably bromine or chlorine.

Among the preferred compounds of formula I are those of the formula

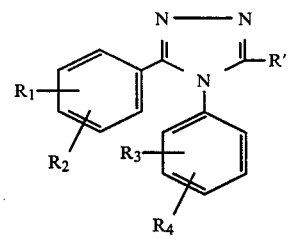

wherein $R_1$, $R_2$, $R_3$ and $R_4$ have the above definitions and R' is selected from the group consisting of alkyl of 1 to 4 carbon atoms, —$CH_2$—COOH and —$CH_2$—$COOAlK_3$, $AlK_3$ is alkyl of 1 to 4 carbon atoms and their non-toxic, pharmaceutically acceptable acid addition salts.

More preferred compounds of the invention are compounds of the formula

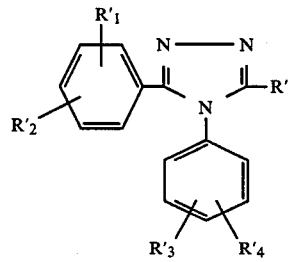

wherein $R_1'$, $R_2'$, $R_3'$ and $R_4'$ have the definitions as $R_1$, $R_2$, $R_3$ and $R_4$ except they may not all be hydrogen and R' has the above definition and their non-toxic, pharmaceutically acceptable acid addition salts.

Among the preferred compounds of formulae I, I' and I'' are those wherein R or R' is alkyl of 2 to 4 carbon atoms, —$CH_2$—COOH or —$CH_2$—$COOAlK_3$ and their non-toxic, pharmaceutically acceptable acid addition salts. Especially preferred are those wherein R or R' is ethyl and their acid addition salts.

Among the preferred compounds of the invention are those of formulae I, I' or I'' wherein $R_1$ or $R_1'$ is hydrogen, those wherein $R_2$ or $R_2'$ is alkoxy of 1 to 4 carbons atoms in any position of the benzene ring, especially 4-methoxy, those wherein $R_3$ or $R_3'$ is hydrogen and $R_4$ or $R_4'$ is methoxy, chloro, —$CF_3$, —$CH_3$ or —$NO_2$ in any position on the benzene ring, especially those wherein $R_3$ or $R_3'$ is 4-methoxy and $R_4$ or $R_4'$ is $CH_3O$—, Cl—, —$CF_3$, —$CH_3$ or $NO_2$ and their non-toxic, pharmaceutically acceptable acid addition salts.

The most preferred compounds of the invention are N,N-dimethyl-4-[5-ethyl-4-(4-methoxyphenyl)-4H-1,2,4-triazol-3-yl]-benzeneamine, 4,4'-[3-ethyl-4H-1,2,4-triazol-4,5-diyl]-N,N,N',N'-tetramethyl-bis-benzeneamine and 3,4-bis(4-methoxyphenol)-5-ethyl-4H-1,2,4- triazole and their nontoxic, pharmaceutically acceptable acid addition salts.

The novel process of the invention for the preparation of the compounds of formula I comprises reacting a compound of the formula

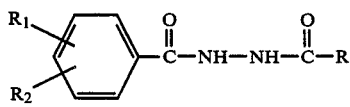

wherein R, $R_1$ and $R_2$ have the above definitions with a compound of the formula

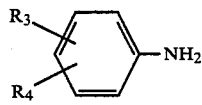

wherein $R_3$ and $R_4$ have the above definitions in the presence of dehydrating agent to obtain the corresponding compound of formula I which, if desired, may be reacted with an acid to form the corresponding acid addition salt. The dehydrating agent is preferably phosphorous trichloride or phosphoric acid anhydride.

The compounds of formula II are generally known compounds which can be made in a known manner such as by the process of Horwitz et al [J. Org., Vol. 19 (1954) p. 194–201] wherein an acid of the formula

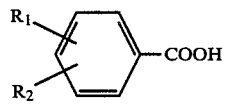

or a functional derivative thereof is reacted with a compound of the formula

wherein R, $R_1$ and $R_2$ have the above definitions.

However, some of the compounds of formula II are novel and are a portion of the invention and these include the 2-(1-oxo-propyl)-hydrazide of 4-methoxy-benzoic acid, the 2-(1-oxo-butyl)-hydrazide of 4-methoxy-benzoic acid, 2-(1-oxopentyl)-hydrazide of 4-methoxy-benzoic acid, the 2-(1-oxo-2-methyl-propyl)-hydrazide of 4-methoxy-benzoic acid, the 2-(1-oxo-propyl)-hydrazide of 4-chloro-benzoic acid, the 2-(1-oxo-propyl)-hydrazide of 3,4-methylenedioxy-benzoic acid and 2-(1-oxo-propyl)-hydrazide of 3,4-dimethoxy-benzoic acid.

A variation of the process of the invention to produce a compound of formula I comprises reacting a compound of the formula

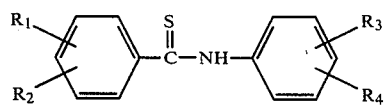

wherein $R_1$, $R_2$, $R_3$ and $R_4$ have the above definitions with hydrazine to obtain a compound of the formula

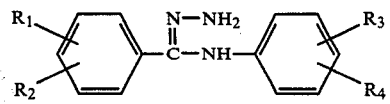

and (A) either reacting the latter with an acid of the formula X—COOH or a functional derivative thereof wherein X is hydrogen or alkyl of 1 to 4 carbon atoms to obtain a compound of the formula

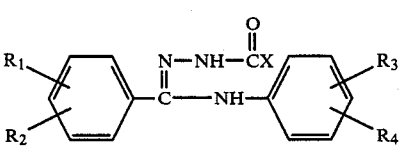

and cyclizing the latter by heating to obtain a compound of the formula

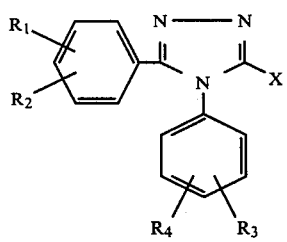

which is a compound of formula I wherein R is hydrogen or alkyl of 1 to 4 carbon atoms which, if desired, may be reacted with an acid to form the corresponding salt or (B) reacting the compound of formula V with a compound of the formula

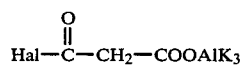

wherein Hal is a halogen and $AlK_3$ has the above definition to obtain the compound of the formula

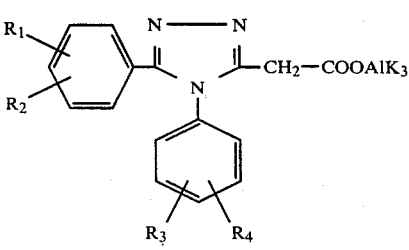

which is the compound of formula I wherein R is —$CH_2$—$COOAlK_3$ which, if desired, may be reacted with an acid to form the salt thereof or treated with an acid hydrolysis agent to obtain a compound of the formula

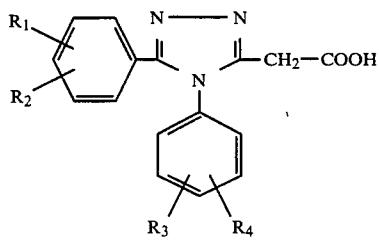

which is the compound of formula I wherein R is —$CH_2$—COOH and if desired, can be reacted with an acid to form the salt thereof.

In a preferred mode of the said process, the functional derivative of the acid X—COOH is its anhydride, ester or acid halide such as the acid chloride and Hal is chlorine. The preferred acid hydrolysis agent is hydrochloric acid.

Obvious variations upon the substitutents $R_1$, $R_2$, $R_3$ and $R_4$ may be used once the compounds of formula I have been prepared. For example, etherification or esterification of a hydroxyl group, cleavage of an alkoxy or acyloxy group to obtain a hydroxyl, transformation of —$NO_2$ to —$NH_2$ or

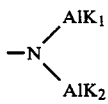

is possible.

The novel intermediate products of the invention also include the compounds of formulae V and VI as well as 4-dimethylamino-4'-methoxy-thiobenzanilide of formula IV.

The compounds of formula IV may be prepared by the process of Ann. Chem., Vol. 716 (1968), p. 209–211) for preparing 4-methoxy-4'-nitro-thiobenzanilide by reacting a compound of the formula

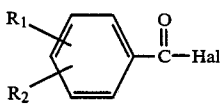

wherein $R_1$ and $R_2$ have the above definition and Hal is a halogen with a compound of the formula

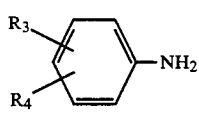

wherein $R_3$ and $R_4$ have the above definitions to obtain a compound of the formula

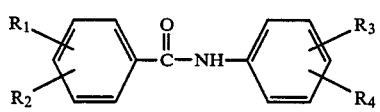

and reacting the latter with phosphorus pentasulfide ($P_2S_5$) in the presence of a tertiary amine such as pyridine to obtain the compound of formula IV.

The novel analgesic compositions of the invention are comprised of an analgesically effective amount of at least one compound of formula I and their non-toxic, pharmaceutically acceptable acid addition salts and an inert pharmaceutical carrier or excipient. The compositions may be in the form of tablets, dragees, gelules, granules, suppositories, injectable solutions or suspensions, pomades, cremes, gels and aerosol preparations made in the usual fashion.

The compositions are useful for the treatment of muscular, articular or nervous pain, dental pain, migraines and for the treatment of rhumatic affections.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers and preservatives.

The novel method of the invention for relieving pain in warm-blooded animals, including humans, comprises administering to warm-blooded animals an analgesically effective amount of at least one compound of formula I and their non-toxic, pharmaceutically acceptable acid addition salts. The compounds may be administered, orally, rectally, parenterally or topically to the skin or mucous. The daily dosage will vary depending upon the compound, the condition being treated and the method of administration. For example, the compound may be orally administered at 1 to 40 mg/kg, per day in the adult. Especially preferred are the compounds of examples 1, 25 and 28.

In the following examples there are described several preferred embodiments to illustrate the invention. However, it should be understood that the invention is not intended to be limited to the specific embodiments.

EXAMPLE 1

3,4-bis-(4-methoxyphenyl)-5-ethyl-4H-1,2,4-triazole

STEP A: 2-(1-oxo-propyl)-hydrazide of 4-methoxy-benzoic acid

A mixture of 20 g of the hydrazide of 4-methoxybenzoic acid [prepared by the process of Beilstein, Vol. 10, I, p. 78] and 75 ml of propionic acid anhydride was heated at 70° C. for 15 minutes and then excess anhydride was distilled. The residue was taken up in petroleum ether (b.p. 60°–80° C.) and the solution was iced and filtered to obtain 25.4 g of 2-(1-oxo-propyl)-hydrazide of 4-methoxy-benzoic acid melting at 135° C.

STEP B: 3,4-bis-(4-methoxyphenyl)-5-ethyl-4H-1,2,4-triazole

A solution of 4.4 ml of phosphorus trichloride in 50 ml of o-dichlorobenzene was added dropwise under an inert atmosphere over 50 minutes to a solution of 33.2 g of anisidine in 100 ml of o-dichlorobenzene and the mixture was heated at 90°~100° C. for 15 minutes. 10 g of the product of Step A were added to the mixture which was heated to 200° C. and refluxed for 3 hours. The mixture was cooled and poured into ice and the mixture was acidified with 50 ml of 2N hydrochloric acid. Water and ether were added to the mixture with stirring and the decanted aqueous phase was washed with ether, treated with activated carbon and filtered. A concentrated sodium hydroxide solution was added dropwise to the filtrate which was then filtered. The recovered product was dried to obtain 10.75 g of 3,4- bis-(4-methoxyphenyl)-5-ethyl-4H-1,2,4-triazole melting at 124°–125° C.

EXAMPLE 2

3,4-bis-(4-methoxyphenyl)-5-ethyl-4H-1,2,4-triazole hydrochloride 2.9 ml of a solution of 5.9N hydrogen chloride in ethanol were added to a solution of 5 g of the product of Example 1, in 5 ml of ethanol and the mixture was stirred while adding isopropyl ether thereto. The mixture was stirred for 24 hours and was filtered. The product was empasted with isopropyl ether, filtered and dried under pressure to obtain 4.4 g of 3,4-bis-(4-methoxyphenyl)-5-ethyl-4H-1,2,4-triazole hydrochloride.

EXAMPLE 3

3-ethyl-5-(4-methoxyphenyl)-4-(2-methylphenyl)-4H-1,2,4-triazole

Using the procedure of Step B of Example 1, 150 ml of o-dichlorobenzene, 28.8 ml of o-toluidine, 4.4 ml of phosphorus trichloride and 10 g of the 2-(1-oxo-propyl)-hydrazide of 4-methoxy-benzoic acid were reacted to obtain 7.4 g of 3-ethyl-5-(4-methoxyphenyl)-4-(2-methylphenyl)-4H-1,2,4-triazole melting at 118° C.

EXAMPLE 4

3-ethyl-5-(4-methoxyphenyl)-4-[3-trifluoromethyl-phenyl]-4H-1,2,4-triazole

Using the procedure of Step B of Example 1, 43.11 g of m-trifluoromethyl-aniline, 150 ml of o-dichlorobenzene, 4.4 ml of phosphorus trichloride and 10 g of 2-(1-oxo-propyl)-hydrazide of 4-methoxy-benzoic acid were reacted to obtain 6.65 g of 3-ethyl-5-(4-methoxy-phenyl)-4-[3-trifluoromethyl-phenyl]-4H-1,2,4-triazole melting at 140° C.

EXAMPLE 5

4-(4-chlorophenyl)-3-ethyl-5-(4-methoxyphenyl)-4H-1,2,4-triazole

Using the procedure of Step B of Example 1, 34.14 g of p-chloroaniline, 150 ml of o-dichlorobenzene, 4.4 ml of phosphorus trichloride and 10 g of 2-(1-oxo-propyl)-hydrazide of 4-methoxy-benzoic acid were reacted to obtain 8.2 g of 4-(4-chlorophenyl)-3-ethyl-5-(4-methoxy-phenyl)-4H-1,2,4-triazole melting at 175°–176° C.

EXAMPLE 6

3-ethyl-5-(4-methoxyphenyl)-4-phenyl-4H-1,2,4-triazole

A mixture of 15 g of 2-(1-oxo-propyl)-hydrazide of 4-methoxy-benzoic acid, 22.5 g of phosphoric acid anhydride and 200 ml of aniline was heated under an inert atmosphere at 160° C. for 2 hours and the aniline was distilled under reduced pressure. The residue was taken up in an ether-aqueous ammonium hydroxide mixture and the decanted ether phase was washed with water, dried and evaporated to dryness. The residue was crystallized by heating in a mixture of 600 ml of cyclohexane and 150 ml of benzene and the solution was treated with activated carbon, was filtered and concentrated to a volume of about 250 ml. The mixture was allowed to crystallize and was filtered to obtain 10 g of 3-ethyl-5-(4-methoxyphenyl)-4-phenyl-4H-1,2,4-triazole melting at 118° C.

EXAMPLE 7

3-ethyl-5-(4-methoxyphenyl)-4-phenyl-4H-1,2,4-triazole hydrochloride 2.85 ml of a 6.4N hydrogen chloride solution in ethanol were added to a solution of 5.1 g of the product of Example 6 in 5.1 ml of ethanol and then isopropyl ether was added thereto. The mixture was filtered and the recovered product was empasted several times with isopropyl ether, filtered and was dried. The product was dissolved in 350 ml of tetrahydrofuran and the solution was filtered and concentrated to a volume of 75 ml. The mixture was cooled, iced and filtered and the recovered product was washed with tetrahydrofuran and dried to obtain 3.3 g of 3-ethyl-5-(4-methoxyphenyl)-4-phenyl-4H-1,2,4-triazole hydrochloride melting towards 150° C. with decomposition.

EXAMPLE 8

3-(4-methoxyphenyl)-4-phenyl-5-methyl-4H-1,2,4-triazole

Using the procedure of Step B in Example 1, 26.3 ml of aniline, 150 ml of o-dichlorobenzene, 4.65 ml of phosphorus trichloride and 10 g of N-(4-methoxybenzoyl)-N'-acetyl-hydrazine [prepared by process of J.Org., Vol. 19 (1954), p. 194–201] were reacted to obtain 7.1 g of 3-(4-methoxyphenyl)-4-phenyl-5-methyl-4H-1,2,4-triazole melting at 140°–141° C.

EXAMPLE 9

3-(4-methoxyphenyl)-4-phenyl-4H-1,2,4-triazole

Using the procedure of Step B of Example 1, 28.2 ml of aniline, 150 ml of o-dichlorobenzene, 4.95 ml of phosphorus trichloride and 10 g of N-anisolyl-N'-formylhydrazine [prepared by process of Ann., Vol. 512 (1934), p. 250] to obtain 7 g of 3-(4-methoxyphenyl)-4-phenyl-4H-1,2,4-triazole melting at 139°–140° C.

EXAMPLE 10

3-ethyl-5-(4-methoxyphenyl)-4-(4-nitrophenyl)-4H-1,2,4-triazole

STEP A:
4-methoxy-N-(4-nitrophenyl)-benzene-carbohydrazonamide

A mixture of 10 g of 4-methoxy-4'-nitrothiobenzanilide [prepared by process of Ann. Chem., Vol. 716 (1968), p. 209–211], 100 ml of ethanol and 15 ml of hydrazine hydrate was heated to reflux and then was allowed to return to room temperature and was filtered. The product was washed with ethanol and dried at 80° C. under reduced pressure to obtain 7.9 g of 4-methoxy-N-(4-nitrophenyl)-benzene-carbohydrazonamide melting at 104° C.

STEP B:
4-methoxy-N-(4-nitrophenyl)-N'-(1-oxo-propyl)-benzene-carbohydrazonamide 0.65 ml of propionic acid anhydride was slowly added to a suspension of 1.4 g of the product of Step A, 14 ml of benzene and 0.4 ml of pyridine and the mixture was stirred for 30 minutes and was vacuum filtered. The product was washed with benzene to obtain 1.45 g of 4-methoxy-N-(4-nitrophenyl)-N'-(1-oxo-propyl)-benzene-carbohydrazonamide melting at 200° C.

STEP C:
3-ethyl-5-(4-methoxyphenyl)-4-(4-nitrophenyl)-4H-1,2,4-triazole 1.2 g of the product of Step B were heated to 250°–300° C. and was then cooled once—gas evolution ceased and the product was washed with ethanol and was vacuum filtered and dried to obtain 0.9 g of 3-ethyl-5-(4-methoxyphenyl)-4-(4-nitrophenyl)-4H-1,2,4-triazole melting at 178° C.

EXAMPLE 11
3,4-bis-(4-methoxyphenyl)-5-propyl-4H-1,2,4-triazole

STEP A: 2-(1-oxo-butyl)-hydrazide of 4-methoxy-benzoic acid 15.6 ml of anhydrous triethylamine were added to a mixture of 12.95 of the hydrazide of 4-methoxy-benzoic acid in 150 ml of toluene and then a solution of 8.56 ml of butyryl chloride in 25 ml of toluene was added thereto. The mixture was stirred at room temperature for 16 hours and then 50 ml of water were added thereto. The mixture was stirred for 2 hours and was vacuum filtered. The product was washed with water and dried to obtain 15.85 g of 2-(1-oxo-butyl)-hydrazide of 4-methoxy-benzoic acid in the form of crystals melting at 130° C.

STEP B:
3,4-bis-(4-methoxyphenyl)-5-propyl-4H-1,2,4-triazole

A mixture of a solution of 31.27 g of anisidine in 100 ml of dichlorobenzene and a solution of 4.1 ml of phosphorous trichloride in 50 ml of dichlorobenzene was heated to 100° C. over 5 minutes and was held at 100° C. for 15 minutes. Then, 10 g of the product of Step A were added to the mixture which was heated to reflux over 15 minutes and held there for 3 hours. The mixture was poured into ice and was filtered and the decanted organic phase was extracted with hydrochloric acid and with water, treated with activated carbon and was filtered. Sodium hydroxide solution was added to the filtrate until the pH was 5 and the mixture was filtered. The recovered product was dissolved in 190 ml of methylene chloride and the solution was dried and filtered. The filtrate was evaporated to dryness and 8.99 g of residue was crystallized from ethyl acetate to obtain after drying 7.45 g of 3,4-bis-(4-methoxyphenyl)-5-propyl-4H-1,2,4-triazole melting at 125°–126° C.

EXAMPLE 12
3-ethyl-4-(3,4-dimethoxyphenyl)-5-(4-methoxyphenyl)-4H-1,2,4-triazole Using the procedure of Step B of Example 11, 41 g of veratrilamine, 4.4 ml of phosphorus trichloride and 10 g of 2-(1-oxo-propyl)-hydrazide of 4-methoxy-benzoic acid were reacted to obtain 19.4 g of raw product which was crystallized from ethyl acetate and then toluene to obtain 3-ethyl-4-(3,4-dimethoxyphenyl)-5-(4-methoxyphenyl)-4H-1,2,4-triazole melting at 150° C.

EXAMPLE 13
3,4-bis-(4-methoxyphenyl)-5-butyl-4H-1,2,4-triazole

STEP A: 2-(1-oxo-pentyl)-hydrazide of 4-methoxy-benzoic acid 9.8 ml of valeryl chloride were added with stirring to a solution of 12.45 g of the hydrazide of 4-methoxybenzoic acid in 40 ml of pyridine and the mixture was stirred for 16 hours. Then, 2 g of ice were added and the mixture was stirred for 15 minutes to destroy excess acid chloride. Water was added to the mixture which was stirred in an ice bath for 30 minutes and was filtered. The crystals were empasted and dried to obtain 17.5 g of 2-(1-oxo-pentyl)-hydrazide of 4-methoxy-benzoic acid melting at 112° C.

STEP B:
3,4-bis-(4-methoxyphenyl)-5-butyl-4H-1,2,4-triazole

Using the procedure of Step B of Example 11, 29.52 g of p-anisidine, 3.85 ml of phosphorus trichloride and 10 g of the product of Step A were reacted to obtain 7.77 g of raw product which was crystallized from ethyl acetate to obtain 4.74 g of 3,4-bis-(4-methoxy-phenyl)-5-butyl-4H-1,2,4-triazole melting at 94° C.

EXAMPLE 14
N,N-dimethyl-4-[3-ethyl-5-(4-methoxyphenyl)-4H-1,2,4-triazole-4-yl]-benzeneamine A mixture of 9.7 g of 3-ethyl-5-(4-methoxyphenyl)-4-(4-nitrophenyl)-4H-1,2,4-triazole, 400 ml of methanol, 150 ml of 37% formaldehyde and 1.5 g of platinum oxide was stirred under a hydrogen atmosphere and after 15 minutes, another 1.5 g of platinum oxide were added thereto. After one hour of stirring, 9.7 g of 9.8% palladized carbon were added thereto and the mixture was filtered. The filtrate was washed with methanol and was evaporated to dryness under reduced pressure. The 12.3 g of residue were chromatographed over silica gel and elution with a 9-1 methylene chloride-methanol mixture yielded 8.8 g of an oil. 4 ml of ethyl acetate were added to the oil and the mixture stood for 16 hours and was vacuum filtered. The recovered crystals were washed and dried to obtain 3.9 g of N,N-dimethyl-4-[3-ethyl-5-(4-methoxyphenyl)-4H-1,2,4-triazole-4yl]-benzeneamine melting at 136° C.

EXAMPLE 15
4-[3-ethyl-5-(4-methoxyphenyl)-4H-1,2,4-triazol-4-yl]-benzenamine A solution of 23 g of stannous chloride in 20 ml of concentrated hydrochloric acid was added all at once to a solution of 10 g of 3-ethyl-5-(4-methoxyphenyl)-4-(4-nitrophenyl)-4H-1,2,4-triazole in 50 ml of concentrated hydrochloric acid and the mixture was vigorously stirred for 2 hours and was filtered. The recovered product was washed with N hydrochloric acid and was added to aqueous 5N sodium hydroxide solution. The mixture was stirred for 2 hours and was filtered and the white crystals were washed and dried at 110° C. under reduced pressure. The 12.5 g of crystals were dissolved in boiling toluene and the mixture was filtered. The filtrate was iced for 16 hours and was vacuum filtered. The product was dried to obtain 3.8 g of 4-[3-ethyl-5-(4-methoxyphenyl)-4H-1,2,4-triazol-4-yl]-benzeneamine in the form of crystals melting at 216° C.

EXAMPLE 16
Ethyl-5-(4-methoxyphenyl)-4-phenyl-4H-1,2,4-triazole-3-acetate

A solution of 5.76 ml of ethyl chloroformyl acetate in 20 ml of tetrahydrofuran was added dropwise at 0° to 5° C. to a solution of 10 g of 4-methoxy-N-phenyl-benzene-carbohydrazonamide [described in Synthesis, 1979, p. 360], 6.2 ml of triethylamine and 50 ml of tetrahydrofuran and the mixture was filtered to remove triethylamine hydrochloride. The tetrahydrofuran was evaporated from the filtrate at 40° C. under reduced pressure and the residue was taken up in 50 ml of toluene. The mixture was refluxed for a few minutes and then stood at 0° to 5° C. for 16 hours and was filtered to obtain 9.2 g of ethyl-5-(4-methoxyphenyl)-4-phenyl-4H-1,2,4-triazole-3-acetate melting at 130°–131° C.

EXAMPLE 17

5-(4-methoxyphenyl)-4-phenyl-4H-1,2,4-triazole-3-acetic acid

A mixture of 4 g of the product of Example 16, 10 ml of 2N sodium hydroxide and 20 ml of ethanol was stirred at 60° C. under argon for 30 minutes and the ethanol was evaporated at 40° C. under reduced pressure. 9.9 ml of 2N hydrochloric acid were added to the aqueous solution and the mixture stood at 0° to 5° C. for 16 hours and was filtered. The recovered product was empasted several times with ice water to remove chlorides and was dried at room temperature under reduced pressure of 0.5 to 1 mmHg to obtain 3.6 g of 5-(4-methoxyphenyl)-4-phenyl-4H-1,2,4-triazole-3-acetic acid.

Analysis: $C_{17}H_{17}N_3O_4$; molecular weight=309.31; Calculated: %C 62.37, %H 5.24, %N 12.84; Found: %C 62.7, %H 5.2, %N 13.1.

EXAMPLE 18

Ethyl 4,5-bis-(4-methoxyphenyl)-4H-1,2,4-triazole-3-acetate 20 ml of hydrazine hydrate were added to a refluxing solution of 20 g of 4-methoxy-N-(4-methoxyphenyl)-benzene-carbothioamide [described in Beilstein B-494] in 120 ml of ethanol to obtain a homogenous solution from which hydrogen sulfide evolved rapidly. After gas evolution ceased, heating was stopped and water was added to the mixture. The mixture was filtered and ethanol was distilled from the filtrate. The resulting insoluble gum was extracted with methylene chloride and the organic phase was washed with water, dried and evaporated to dryness under reduced pressure at 30°–35° C.

The resulting residue was added to 350 ml of tetrahydrofuran and 13.7 ml of triethylamine were added thereto followed by addition of a solution of 9.9 ml of ethyl chloroformyl acetate in 20 ml of dry tetrahydrofuran. The mixture was stirred for 90 minutes at 21° C. and was filtered. The filter was washed with tetrahydrofuran and the filtrate was evaporated to dryness under reduced pressure at 30°–35° C. The gummy residue was dissolved in 200 ml of toluene and the solution was refluxed for 20 minutes and was evaporated to dryness under reduced pressure. The 25.636 g of residue were triturated with ether, iced for one hour and vacuum filtered. The recovered crystals were washed 3 times with a little ether and were dried to obtain 20.285 g of a product melting at 144°~145° C.

The said product was dissolved in 250 ml of ethyl acetate and the solution was treated with activated carbon at reflux and was concentrated to a volume of 50 ml of atmosphere pressure. The mixture was iced and vacuum filtered and the crystals were washed with ethyl acetate and dried at 100° C. under reduced pressure to obtain 16.28 g of ethyl 4,5-bis-(4-methoxyphenyl)-4H-1,2,4-triazole-3-acetate melting at 156° C.

EXAMPLE 19

3-isopropyl-4,5-bis-(4-methoxyphenyl)-4H-1,2,4-triazole

STEP A: 2-(1-oxo-2-methyl-propyl)-hydrazide of 4-methoxy-benzoic acid

A solution of 14.2 ml of isobûtynyl chloride in 20 ml of tetrahydrofuran was added to a solution of 20 g of the hydrazide of 4-methoxy-benzoic acid, 200 ml of tetrahydrofuran and 37.5 ml of triethylamine and the suspension was stirred at room temperature for 3 hours. 100 ml of water were added to the mixture which was then extracted with methylene chloride. The extract was evaporated to dryness under reduced pressure and the residue was crystallized from ethanol to obtain 15.7 g 2-(1-oxo-2-methyl-propyl)-hydrazide of 4-methoxy-benzoic acid melting at 162° C.

STEP B: 3-isopropyl-4,5-bis-(4-methoxyphenyl)-4H-1,2,4-triazole

A solution of 4.4 ml of phosphorus trichloride in 50 ml of o-dichlorobenzene was added over 20 minutes to a solution of 31.6 g of p-anisidine in 100 ml of o-dichlorobenzene and the mixture was heated at 110° C. for 30 minutes and was allowed to cool to 50° C. Then, 10 g of the product of Step A were added to the mixture which was then refluxed for 3 hours, cooled to 60° C. and poured into a mixture of ice and 2N hydrochloric acid. The mixture was stirred for 30 minutes and was filtered and the filter was washed with ether. The filtrate was extracted with ether and the limpid solution was adjusted to a pH of 5 by addition of concentrated sodium hydroxide solution. The mixture was stirred for 30 minutes and was vacuum filtered. The product was washed and dried to obtain 13.8 g of product which was crystallized from ethyl acetate to obtain 8 g of 3-isopropyl-4,5-bis-(4-methoxyphenyl)-4H-1,2,4-triazole melting at 162° C.

EXAMPLE 20

3-ethyl-4-(4-chlorophenyl)-5-(4-methoxyphenyl)-4H-1,2,4-triazole

STEP A: 2-(1-oxo-propyl)-hydrazide of 4-chlorobenzoic acid 4.78 ml of propionyl chloride were added at less than 50° C. to a solution of 8.525 g of the hydrazide of 4-chlorobenzoic acid and 25 ml of anhydrous pyridine and the mixture was stirred at room temperature for 15 hours and was added to ice. The mixture was stirred for 15 minutes to destroy excess acid chloride and then 125 ml of distilled water was slowly added thereto to cause precipitation. The mixture was stirred at 0° to 5° C. for 30 minutes and was filtered. The product was washed with water and dried at 90° C. under reduced pressure to obtain 9.21 g of product melting at 201° C. The product was crystallized from ethanol to obtain 6.77 g of 2-(1-oxo-propyl)-hydrazide of 4-chlorobenzoic acid melting at 206° C.

STEP B: 3-ethyl-4-(4-chlorophenyl)-5-(4-methoxyphenyl)-4H-1,2,4-triazole

Using the procedure of Step B of Example 19, the product of Step A and p-anisidine were reacted to obtain 3-ethyl-4-(4-chlorophenyl)-5-(4-methoxyphenyl)-4H-1,2,4-triazole melting at 162° C.

EXAMPLE 21

3-(3,4-methylenedioxy-phenyl)-5-ethyl-4-(4-methoxyphenyl)-4H-1,2,4-triazole

STEP A: 2-(1-oxo-propyl)-hydrazide of 3,4-methylenedioxy benzoic acid

A solution of 23 g of the hydrazide of 3,4-methylenedioxy-benzoic acid [described in J. Org. Chem., Vol. 20, (1955), p.855], 60 ml of propionic acid anhydride and 50 ml of pyridine was stirred at 70° C. for 30 minutes and was then poured over ice. The mixture was vacuum filtered and the product was washed with water and dried at 90° C. under reduced pressure. The 30.7 g of product melting at 138° C. was crystallized from ethyl acetate to obtain 24.1 g of 2-(1-oxo-propyl)-hydrazide of 3,4-methylenedioxy benzoic acid melting at 158° C.

STEP B: 3-(3,4-methylenedioxyphenyl)-5-ethyl-4-(4-methoxyphenyl)-4H-1,2,4-triazole Using the procedure of Step B of Example 19, the product of Step A and anisidine were reacted to obtain 3-(3,4-methylenedioxyphenyl)-5-ethyl-4-(4-methoxyphenyl)-4H-1,2,4-triazole which after crystallization from absolute alcohol melted at 197° C.

EXAMPLE 22

3,4-diphenyl-5-methyl-4H-1,2,4-triazole

Using the procedure of Step B of Example 19, 10 g of 2-(1-oxo-ethyl)-hydrazide of benzoic acid, 31.35 g of aniline and 8.5 g of phosphorus trichloride were reacted to obtain 9.47 g of 3,4-diphenyl-5-methyl-4H-1,2,4-triazole melting at 163° C.

EXAMPLE 23

N,N-dimethyl-4-(4-phenyl-4H-1,2,4-triazole-3-yl)-benzeneamine

Using the procedure of Example 18, 4 g of 4-dimethylamino-N-phenyl-benzene-carbohydrazonaminde [Ber. Vol. 96 (1963), p. 2996] and 130 ml of ethyl formate were reacted to obtain 755 mg of N,N-dimethyl-4-(4-phenyl-4H-1,2,4-triazole)-benzeneamine melting at 226° C.

EXAMPLE 24

N,N-dimethyl-4-[5-ethyl-4-(4-nitrophenyl)-4H-triazol-3yl]-benzeneamine

STEP A: 4-dimethylamine-N-(4-nitrophenyl)-benzenecarbothiamide

A mixture of 55.6 g of 4-dimethylamine-benzoyl chloride prepared by reacting thionyl chloride and 4-dimethyl-amino-benzoic acid in carbon tetrachloride, 4.3 g of p-nitroaniline and 210 ml of pyridine was refluxed for 2 hours and the mixture was cooled to 0° C. 100 g of phosphorus pentasulfide were added to the mixture which was then refluxed for 2 hours. The mixture was cooled to 40° C. and was poured into an ice-hydrochloric acid mixture. The mixture was stirred at room temperature for one hour and was vacuum filtered. The product was washed with water and dried to obtain 187.3 g of product which was added to N sodium hydroxide solution. The mixture was stirred for one hour and filtered and the product was washed with water and dried to obtain 84 g of 4-dimethylamino-N-(4-nitrophenyl)-benzenecarbothiamide melting at 210° C.

STEP B: 4-dimethylamino-N'-(4-nitrophenyl)-benzenecarbohydrazonamide

A suspension of 30 g of the product of Step A and 180 ml of ethanol was heated to reflux and 30 ml of hydrazine hydrate were added thereto. The mixture was refluxed for 15 minutes and then 180 ml of distilled water were added thereto. The mixture was cooled to 10° C. and was vacuum filtered. The product was washed with water and dried to obtain 19 g of 4-dimethylamino-N'-(4-nitrophenyl)-benzenecarbohydrazonamide melting at 174° C.

STEP C: N,N-dimethyl-4-[5-ethyl-4-(4-nitrophenyl)-4H-triazol-3-yl]-benzeneamine 5.8 ml of propionyl chloride were poured into a solution of 19 g of the product of Step B, 200 ml of anhydrous tetrahydrofuran and 17.6 ml of triethylamine and the mixture was filtered. The filter was washed with tetrahydrofuran and the filtrate was evaporated to dryness under reduced pressure. The residue was dissolved in toluene and the mixture was refluxed for 30 minutes and then was evaporated to dryness. The oil residue was dissolved in hot ethyl acetate and the solution was cooled and filtered to obtain 3.25 g of product melting at 183°–184° C. The filtrate was chromatographed over silica gel and eluted with a 95-5 methylene chloride-methanol mixture to obtain 7.7 g of N,N-dimethyl-4-[5-ethyl-4-(4-nitrophenyl)-4H-triazol-3-yl]-benzeneamine.

EXAMPLE 25

4,4'-[3-ethyl-4H-1,2,4-triazol-4,5-diyl]-N,N,N',N'-tetramethyl-bis-benzeneamine

A mixture of 7.3 g of N,N-dimethyl-4-[5-ethyl-4-nitrophenyl)-4H-1,2,4-triazol-3-yl]-benzeneamine, 300 ml of methanol, 40 ml of formaldehyde and 1.4 g of platinum oxide was hydrogenated until hydrogen absorption ceased and was then filtered. The filter was washed with methylene chloride and the filtrate was evaporated to dryness under reduced pressure. The 8 g of oil residue were chromatographed over silica gel and eluted with a 95-5 methylene chloride-methanol mixture to obtain 6.7 g of an oil which slowly crystallized from ethyl acetate to obtain 4,4'-[3-ethyl-4H-1,2,4-triazol-4,5-diyl]-N,N,N',N'-tetramethyl-bis-benzeneamine melting at 178° C. and then 186° C.

EXAMPLE 26

4,4'-(3-ethyl-4H-1,2,4-triazol-4,5-diyl)-bis-phenol

A solution of 6 g of 3,4-bis-(4-methoxyphenyl)-5-ethyl-4H-1,2,4-triazole and 25 ml of a solution of hydrobromic acid at 48% was refluxed with stirring for one hour and the hydrobromic acid was distilled under reduced pressure. The crystalline residue was dissolved in 30 ml of hot water and ammonium hydroxide was added thereto until the pH was alkaline. The mixture stood overnight with stirring and was vacuum filtered. The product was washed with water and dried at 90° C. under reduced pressure to obtain a product which was crystallized from dimethylformamide. The mixture was iced for one hour and was vacuum filtered. The product was washed with a 3-4 dimethylformamide-water mixture and dried to obtain 4.395 g of 4,4'-(3-ethyl-4H-1,2,4-triazol-4,5-diyl)-bis-phenol melting at 317°–318° C.

EXAMPLE 27

4-(3-ethyl-4-phenyl-4H-1,2,4-triazol-5-yl)-phenol

A solution of 3.86 g of 3-ethyl-5-(4-methoxyphenyl)-4-phenyl-4H-1,2,4-triazole and 20 ml of a hydrobromic acid solution at 48% was refluxed with stirring for one hour and the mixture was evaporated to dryness under reduced pressuure. The residue was dissolved in 20 ml of hot water and ammonium hydroxide was added until the pH was alkaline. The mixture was stood overnight with stirring and was vacuum. The product was washed with water and dried at 90° C. under reduced pressure. The 3.65 g of product were crystallized from methanol and the mixture was iced and vacuum filtered. The crystals were washed by empasting with methanol and were dried at 90° C. under reduced pressure to obtain 3.245 g of 4-(3-ethyl-4-phenyl-4H-1,2,4-triazol-5-yl)-phenol melting at 275° C.

EXAMPLE 28

N,N-dimethyl-4-[5-ethyl-4-(4-methoxyphenyl)-4H-1,2,4-triazol-3-yl]-benzeneamine

STEP A:
4-dimethylamino-N-(4'-methoxyphenyl)-benzenecarbothiamide 13.6 g of p-anisidine were added to a solution of 22.2 g of 4-dimethylamino-benzoic acid chloride in 84 ml of anhydrous pyridine and the mixture was refluxed for one hour and cooled to 30° C. 33 g of phosphorus pentasulfide were added to the mixture which was refluxed for 2 hours and was then poured into an ice water-concentrated hydrochloric acid mixture. The mixture was stirred for one hour and was vacuum filtered and the product was washed with 0.1N hydrochloric acid. A mixture of the product and 300 ml of N sodium hydroxide solution was stirred for one hour and was vacuum filtered. The product was washed with water and dried to obtain 13.5 g of 4-dimethylamino-N-(4'-methoxyphenyl)-benzenecarbothiamide melting at 192° C.

STEP B:
N,N-dimethyl-4-[5-ethyl-4-(4-methoxyphenyl)-4H-1,2,4-triazol-3-yl]-benzeneamine A suspension of 8.5 g of the product of Step A and 50 ml of ethanol was heated to reflux and 9 ml of hydrazine hydrate were added thereto. The mixture was refluxed for 30 minutes and ice water was then added thereto. The mixture was extracted with methylene chloride and the organic phase was evaporated to dryness under reduced pressure. The 10 g of residue was taken up in 140 ml of tetrahydrofuran and 17 ml of triethylamine were added thereto. 11.5 ml of propionyl chloride were added to the mixture over 10 minutes and the mixture was stirred for 30 minutes and was vacuum filtered. The filter was washed with tetrahydrofuran and the filtrate was evaporated to dryness under reduced pressure. The oil residue was taken up in 200 ml of toluene and the solution was refluxed for 2 hours and then evaporated to dryness under reduced pressure. The residue was added to a mixture of 100 ml of hydrochloric acid and 200 ml of water and the aqueous phase was extracted with ether and was filtered. The pH of the filtrate was adjusted to 6 by addition of concentrated sodium hydroxide solution and the mixture was extracted with methylene chloride to obtain 7.1 g of gum. The latter was chromatographed over silica gel and was eluted with a 95-5 methylene chloride-methanol mixture to obtain 2.4 g of N,N-dimethyl-4-[5-ethyl-4-(4-methoxyphenyl)-4H-1,2,4-triazol-3-yl]-benzeneamine which melted at 148° C. after crystallization from a 1-1 toluene-ether mixture.

EXAMPLE 29

3-ethyl-5-(3,4-dimethoxyphenyl)-4-(4-methoxyphenyl)-4H-1,2,4-triazole

STEP A: 2-(1-oxo-propyl)-hydrazide of 3,4-dimethoxy-benzoic acid

A mixture of 16.2 g of the hydrazide of 3,4-dimethoxy-benzoic acid (J.A.C.S., 1970, p. 1901) and 40 ml of propionic acid anhydride was heated at 65° C. for 30 minutes and excess acid anhydride was evaporated under reduced pressure. The reaction mixture was poured into a solution of 200 ml of methylene chloride and 50 ml of ethyl acetate and 550 ml of solvent were distilled at normal pressure. The mixture was iced and vacuum filtered and the crystals were washed with ethyl acetate and dried to obtain 20.2 g of 2-(1-oxo-propyl)-hydrazide of 3,4-dimethoxy-benzoic acid melting at 142° C.

STEP B:
3-ethyl-5-(3,4-dimethoxyphenyl)-4-(4-methoxyphenyl)-4H-1,2,4-triazole Using the procedure of Example 11, 29.29 g of p-anisidine, 382 ml of phosphorus trichloride and 10 g of the product of Step A were reacted to obtain 15.11 g of raw 3-ethyl-5-(3,4-dimethoxyphenyl)-4-(4-methoxyphenyl)-4H-1,2,4-triazole which melted at 148° C. after crystallization from ethyl acetate.

EXAMPLE 30

Tablets were prepared containing 50 mg of the product of Example 1 or Example 25 and sufficient excipient of lactose, talc, starch and magnesium stearate to obtain a final tablet weight of 350 mg.

PHARMACOLOGICAL DATA

A. Analgesic activity

The test used was that of Singmund et al [Proc. Soc. Exp. Biol. and Med., Vol. 95 (1957), p. 729] wherein intraperitoneal administration of phenyl benzoquinone to mice provoked repeated stretching and twisting movements which are eliminated or prevented by analgesics. The syndrome is considered as an exteriorization of a diffuse abdominal pain. A solution of 0.02% by weight of phenyl benzoquinone in water containing 4% of ethanol was injected into the mice at a volume of 0.25 ml and the test compound of Example 1 was orally administered 30 minutes before the injection. The mice were fasted for 6 hours and the stretchings were observed and counted for each mouse for a 15 minute observation period beginning 5 minutes after the phenylbenzoquinone injection. The results expressed as the $AD_{50}$, the dose which permitted a lessening of 50% of the number of stretchings as compared to the control mice were determined to be 7 mg/kg for the compound of Example 1.

B. Analgesic test

This test was based on the procedure of Koster et al [Fed. Proc., Vol. 18 (1959), p. 412] wherein mice received an intraperitoneal injection of acetic acid to provoke repeated stretching and twisting movements which is considered to be manifestation of a diffuse abdominal pain which is diminished or eliminated by analgesics. The acetic acid was injected at a dose of 100 mg/kg or 1 ml of an aqueous solution at 1% per 100 g of body weight to female mice weighing 20 to 22 g after fastening for 7 hours. The product of Examples 25 or 28 was orally administered to the mice 30 minutes before the acetic acid injection to groups of 10 mice and each test included a control group which received only the vehicle, 5 minutes after the acetic acid injection, the number of stretchings and twistings for each mouse was counted over a 15 minutes period.

The analgesic effect was expressed as the percentage of protection as compared to the movements of the control mice which received the acetic acid only and the $AD_{50}$, the dose which lessened by 50% the number of stretchings, was determined to be about 4 mg/kg for the products of Examples 25 and 28.

Various modifications of the products and methods of the invention may be made without departing from the spirit or scope thereof and it should be understood that the invention is intended to be limited only as defined in the appended claims.

We claim:

1. A compound selected from the group consisting of 4H-1,2,4-triazoles of the formula

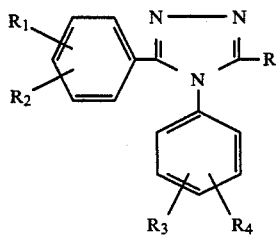

wherein $R_1$, $R_3$ and $R_4$ may be in different positions of the benzene rings and are individually selected from the group consisting of hydrogen, —OH, alkyl of 1 to 4 carbon atoms, alkoxy of 1 to 4 carbon atoms, halogen, —$CF_3$, —$NO_2$, —$NH_2$ and —NH—AlK and

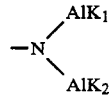

and AlK, $AlK_1$ and $AlK_2$ are alkyl of 1 to 4 carbon atoms or $R_1$ and $R_2$ together and/or $R_3$ and $R_4$ together are methylenedioxy, $R_2$ is alkoxy of 1 to 4 carbon atoms, R is selected from the group consisting of hydrogen, alkyl of 1 to 4 carbon atoms, —$CH_2$—COOH and —$CH_2$—COOAlK$_3$ and AlK$_3$ is alkyl of 1 to 4 carbon atoms and their non-toxic, pharmaceutically acceptable acid addition salts.

2. A compound of claim 1 wherein R is selected from the group consisting of alkyl of 1 to 4 carbon atoms, —$CH_2$—COOH and —$CH_2$—COOAlK$_3$ and AlK$_3$ is alkyl of 1 to 4 carbon atoms.

3. A compound of claim 1 wherein R is selected from the group consisting of alkyl of 2 to 4 carbon atoms, —$CH_2$—COOH and —$CH_2$—COOAlK$_3$ and AlK$_3$ is alkyl of 1 to 4 carbon atoms.

4. A compound of claim 1 wherein R is ethyl.

5. A compound of claim 1 wherein $R_1$ is hydrogen.

6. A compound of claim 1 wherein $R_2$ is 4-methoxy.

7. A compound of claim 1 wherein $R_3$ is hydrogen and $R_4$ is selected from the group consisting of $CH_3O$—, Cl—, —$CF_3$, —$CH_3$ and —$NO_2$.

8. A compound of claim 1 wherein $R_3$ is 4-methoxy and $R_4$ is selected from the group consisting of $CH_3O$—, Cl—, —$CF_3$, —$NO_2$ and $CH_3$—.

9. A compound of claim 1 selected from the group consisting of 3,4-bis-(4-methoxyphenyl)-5-ethyl-4H-1,2,4-triazole and its non-toxic, pharmaceutically acceptable acid addition salts.

10. A compound of claim 1 selected from the group consisting of N,N-dimethyl-4-[3-ethyl-5-(4-methoxyphenyl)-4H-1,2,4-triazole-4-yl]-benzeneamine and its non-toxic, pharmaceutically acceptable acid addition salts.

11. An analgesic composition comprising an analgesically effective amount of at least one compound of claim 1 and an excipient.

12. A composition of claim 11 wherein R is selected from the group consisting of alkyl of 1 to 4 carbon atoms, —$CH_2$—COOH and —$CH_2$—COOAlK$_3$ and AlK$_3$ is alkyl of 1 to 4 carbon atoms.

13. A composition of claim 11 wherein R is selected from the group consisting of alkyl of 2 to 4 carbon atoms, —$CH_2$—COOH and —$CH_2$—COOAlK$_3$ and AlK$_3$ is alkyl of 1 to 4 carbon atoms.

14. A composition of claim 11 wherein R is ethyl.

15. A composition of claim 11 wherein $R_1$ is hydrogen.

16. A composition of claim 11 wherein $R_2$ is 4-methoxy.

17. A composition of claim 11 wherein $R_3$ is hydrogen and $R_4$ is selected from the group consisting of $CH_3O$—, Cl—, —$CF_3$, $CH_3$— and —$NO_2$.

18. A composition of claim 11 wherein $R_3$ is 4-methoxy and $R_4$ is selected from the group consisting of $CH_3O$—, Cl—, —$CF_3$—, —$NO_2$ and $CH_3$—.

19. A composition of claim 11 wherein the active compound is selected from group consisting of 3,4-bis-(4-methoxyphenyl)-5-ethyl-4H-1,2,4-triazole and its non-toxic, pharmaceutically acceptable acid addition salts.

20. A method of relieving pain in warm-blooded animals comprising administering to warm-blooded animals an analgesically effective amount of at least one compound of claim 1.

21. A method of claim 20 wherein R is selected from the group consisting of alkyl of 1 to 4 carbon atoms, —$CH_2$—COOH and —$CH_2$—COOAlK$_3$ and AlK$_3$ is alkyl of 1 to 4 carbon atoms.

22. A method of claim 20 wherein R is selected from the group consisting of alkyl of 2 to 4 carbon atoms, —$CH_2$—COOH and —$CH_2$—COOAlK$_3$ and AlK$_3$ is alkyl of 1 to 4 carbon atoms.

23. A method of claim 20 wherein R is ethyl.

24. A method of claim 20 wherein $R_1$ is hydrogen.

25. A method of claim 20 wherein $R_2$ is 4-methoxy.

26. A method of claim 20 wherein $R_3$ is hydrogen and $R_4$ is selected from group consisting of $CH_3O$—, Cl—, —$CF_3$, $CH_3$— and —$NO_2$.

27. A method of claim 20 wherein $R_3$ is 4-methoxy and $R_4$ is selected from the group consisting of $CH_3O$—, Cl—, —$CF_3$—, —$NO_2$ and $CH_3$—.

28. A method of claim 20 wherein the active compound is selected from the group consisting of 3,4-bis-(4-methoxyphenyl)-5-ethyl-4H-1,2,4-triazole and its non-toxic, pharmaceutically acceptable acid addition salts.

* * * * *